United States Patent
Peters

(10) Patent No.: US 9,539,369 B2
(45) Date of Patent: Jan. 10, 2017

(54) LONG-ACTING LIMUS FORMULATION ON BALLOON CATHETERS

(71) Applicant: InnoRa GmbH, Berlin (DE)

(72) Inventor: Daniel Peters, Berlin (DE)

(73) Assignee: InnoRa GmbH, Berlin (DE)

( * ) Notice: Subject to any disclaimer, the term of this patent is extended or adjusted under 35 U.S.C. 154(b) by 0 days.

(21) Appl. No.: 15/022,597

(22) PCT Filed: Sep. 12, 2014

(86) PCT No.: PCT/EP2014/069517
§ 371 (c)(1),
(2) Date: Mar. 17, 2016

(87) PCT Pub. No.: WO2015/039969
PCT Pub. Date: Mar. 26, 2015

(65) Prior Publication Data
US 2016/0228617 A1    Aug. 11, 2016

(30) Foreign Application Priority Data
Sep. 18, 2013 (DE) .......... 10 2013 110 294

(51) Int. Cl.
A61L 29/16    (2006.01)
A61M 25/10    (2013.01)

(52) U.S. Cl.
CPC ............ *A61L 29/16* (2013.01); *A61M 25/104* (2013.01); *A61M 25/1029* (2013.01); *A61L 2300/416* (2013.01); *A61L 2300/63* (2013.01); *A61L 2420/02* (2013.01); *A61M 2025/105* (2013.01); *A61M 2025/1031* (2013.01)

(58) Field of Classification Search
CPC ............... A61L 29/16; A61L 2300/416; A61L 2300/63; A61L 2420/02; A61M 25/1029; A61M 25/104; A61M 2025/103; A61M 2025/105
See application file for complete search history.

(56) References Cited

U.S. PATENT DOCUMENTS

| | | | |
|---|---|---|---|
| 8,439,686 B2 | 5/2013 | Zayfert et al. | |
| 2008/0118544 A1 | 5/2008 | Wang | |
| 2010/0324648 A1 | 12/2010 | Scheller et al. | |
| 2010/0331816 A1 | 12/2010 | Dadino et al. | |
| 2011/0008260 A1 | 1/2011 | Flanagan et al. | |
| 2011/0009618 A1 | 1/2011 | Viswanath et al. | |
| 2012/0015442 A1 | 1/2012 | Gilbert et al. | |
| 2013/0053947 A1 | 2/2013 | Kangas et al. | |
| 2013/0123695 A1 | 5/2013 | Hoffmann et al. | |

FOREIGN PATENT DOCUMENTS

| | | |
|---|---|---|
| WO | WO-2006/039237 A1 | 4/2006 |
| WO | WO-2010/086863 A2 | 8/2010 |
| WO | WO-2010/124098 A2 | 10/2010 |
| WO | WO-2010/129328 A2 | 11/2010 |
| WO | WO-2011/008393 A2 | 1/2011 |
| WO | WO-2011/147408 A2 | 12/2011 |
| WO | WO-2013/059509 A1 | 4/2013 |

OTHER PUBLICATIONS

Search Report and Written Opinion in International Application No. PCT/EP2014/069517 dated Nov. 24, 2014, 12 pages.
International Preliminary Report on Patentability in International Application No. PCT/EP2014/069517 dated Jan. 15, 2016, 7 pages.
Cremers et al., "Inhibition of Neointimal Hyperplasia with a Novel Zotarolimus Coated Balloon Catheter", Clin Res Cardiol, vol. 101, 2012, pp. 469-476.
Takimura et al., "Estudo da Dose Excipiente:Fármaco com Avaliação da Hiperplasia Neointimal por Tomografia de Coerência Óptica e Histopatologia em Artérias Coronárias Porcinas após o Emprego do Balão Eluidor de Sirolimus", Rev Bras Cardiol Invasiva, 20(2), 2012, pp. 133-139.
Schmehl et al., "Balloon Coating with Rapamycin Using an On-Site Coating Device", Cardiovasc Intervent Radiol, vol. 36, 2013, pp. 756-763.
Granada et al., "Vascular Response to Zotarolimus-Coated Balloons in Injured Superficial Femoral Arteries of the Familial Hypercholesterolemic Swine", Circ Cardiovasc Interv. 4, 2011, pp. 447-455, http://circinterventions.ahajournals.org/, retrieved from the internet on Mar. 16, 2016.
Gray et al., "Drug-Coated Balloons for the Prevention of Vascular Restenosis", Circulation 121(24), Jun. 22, 2010, pp. 2672-2680.
Tellez et al., "Acute Delivery and Long Term Retention of Sirolimus Nanoparticles Using a Novel Porous Angioplasty Balloon in the Porcine Coronary Model", JACC 60/17/Suppl B: B173, 2012, 1 page, http://content.onlinejacc.org/, retrieved from the internet on Mar. 16, 2016.
Farah et al., "Crystalline Coating of Rapamycin Onto a Stent: Process Development and Characterization", International Journal of Pharmaceutics 445, 2013, pp. 20-28.

*Primary Examiner* — Michael C Miggins
(74) *Attorney, Agent, or Firm* — Marshall, Gerstein & Borun LLP

(57) ABSTRACT

The invention relates to balloon catheters having a polymer-free coating on the balloon surface, said coating comprising at least one limus substance in crystalline form, and to methods for the polymer-free coating of balloon surfaces, in particular balloon catheters, with crystalline limus substances.

18 Claims, No Drawings

LONG-ACTING LIMUS FORMULATION ON BALLOON CATHETERS

Within a few weeks or months after reopening constricted or stenosed arteries and other passages in the body by various mechanical or thermal methods, a renewed stenosis often develops due to excessive proliferation of tissue. This process and how to prevent it have been investigated with particular care on the coronary arteries. Since approximately 2002, drug-eluting stents have been implanted to keep the lumen of the coronary arteries open after being widened to the original diameter, not only through an adequate radial force but also to limit the growth of the constituents of the vascular wall into the lumen through the struts of the stent by sustained release of proliferation-inhibiting pharmaceutical drugs.

Two substance classes were originally used successfully for coating stents: macrolide lactones, such as rapamycin (=sirolimus), everolimus, biolimus and zotarolimus, which bind to mTOR (mammalian target of rapamycin) and thereby inhibit cell division, as well as paclitaxel, a taxan that stabilizes microtubuli and also inhibits cell division. Since then, the macrolide lactones, also known as limus substances, have been used successfully in coating stents.

In addition to coronary stents and as an alternative to treatment of other arteries, drug-coated balloon catheters have become available in the meantime. As in the case of a stent, the pharmaceutical drug serves to prevent re-stenosis of the vessels that have been dilated by means of balloon angioplasty. However, the pharmaceutical drug is dispensed by the balloon only during the short period of time of balloon expansion (<1 min to max. 5 min in peripheral vessels). In contrast with stents, paclitaxel is the dominant active ingredient. Limus substances have been investigated in animal experiments for many years but have so far yielded only unsatisfactory, contradictory or even poorly reproducible results (B. Cremers, J. L. Toner, L. B. Schwartz, R. von Oepen, U. Speck, N. Kaufels, Y. P. Clever, D. Mahnkopf, M. Böhm, B. Scheller. Inhibition of Neointimal Hyperplasia with a Novel Zotarolimus-Coated Balloon Catheter. Clin Res Cardiol. 2012; 101:469-76; U.S. 20100331816; C. K. Takimura, M. Z. Galon, P. Sojitra, M. Doshi, V. Aiello, P. S. Gutierrez, J. Carvalho, S. K. Ferreira, M. J. F. Chaves, F. R. M. Laurindo, P. A. Lemos. Estudo da Doise Excipiente: Fármaco com Avaliação da Hiperplasia Neointimal par Tomografia de Coerência Óptica e Histopatologia em Artérias Coronárias Porcinas após o Emprego do Balão Eluidor de Sirolimus. Rev Bras Cardiol Invasiva. 2012; 20(2); 133-9; J. Schmehl, J. von der Ruhr, M. Dobratz, R. Kehlbach, I. Braun, T.-O. Greiner, C. D. Claussen, B. Behnisch. Balloon Coating with Rapamycin Using an On-site Coating Device. Cardiovasc Intervent Radial 2013; 36; 756-763; J. F. Granada, K. Milewski, H. Zhao, J. J. Stankus, A. Tellez, M. S. Aboodi, B. S.; G. L. Kaluza, C. G. Krueger, R. Virmani, M. D.; L. B. Schwartz, A. Nikanorov. Vascular Response to Zotarolimus-Coated Balloons in Injured Superficial Femoral Arteries of the Familial Hypercholesterolemic Swine Circ Cardiovasc Interv. 2011; 4; 447-455). So far, there has not been any proof of a clinical effect with regard to inhibiting restenosis.

The cause of the low efficacy of limus substances on balloon catheters is seen in the low transfer of drugs to the vascular wall and the fact that the concentration of active ingredient in the vascular wall is not maintained for a long enough period of time to produce the desired effect (W. A. Gray, J. F. Granada. Drug-Coated Balloons for the Prevention of Vascular Restenosis. Circulation. 2010 Jun. 22; 121(24): 2672-2680, see pages 2673-2674, FIG. 1; A. Tellez, P. Buszman, M. Afari, T. Palmieri, Y. Cheng, W. Rate, S. Stone, G. Conditt, Y.-F. Keng, B. Bingham, W. Baumbach, D. Sherman, G. Kaluza, J. Granada. Acute Delivery and Long-Term Retention of Sirolimus Nanoparticles Using a Novel Porous Angioplasty Balloon in the Porcine Coronary Model. JACC 2012; 60/17/Suppl B: B173).

In comparison with paclitaxel, it has been possible to achieve initially similar active ingredient concentrations in the arterial wall, but the active ingredient concentration declines much more rapidly, so that the concentrations are much lower at a later point in time.

As is the case with many other pharmaceutical drugs, limus substances are known to occur in both amorphous form (e.g., WO2006039237 A1, WO2010129328 A1) and crystalline form. Both forms have certain advantages and disadvantages, depending on the application.

It is known that crystals of active ingredients, specifically also crystals of limus active ingredients, dissolve more slowly than the amorphous substance. This fact has been utilized to delay the release of rapamycin from stent surfaces. A complicated procedure has been described for coating stents with suitable rapamycin crystals (S. Farah, W. Khan, A. J. Domb, Crystalline Coating of Rapamycin onto a Stent: Process Development and Characterization. Int J Pharmaceutics 2013; 445:20-28).

Investigations of stent coating cannot be applied simply to coating angioplasty balloons. The stent is introduced into the artery and remains there. In the case of the stent, the substance may be dissolved slowly from a stable surface having a plurality of layers of crystals. However, the balloon comes in contact with the vascular wall only for a very short period of time. The required dose must then enter the vascular wall. If the active ingredient is not already dissolved, then individual particles or crystals, which are accessible to the solvent from all sides, are dissolved.

There is some debate about the use of crystals for coating balloon catheters because of the risk of an embolism, and in some cases this practice is rejected. Amorphous coatings are preferred (WO 2011/147408, page 4, lines 14-24).

The object of the present invention is to coat balloons of balloon catheters in a certain manner with representatives from the class of macrolide lactones (macrolides, also macrolactones), in particular limus substances, so that the coating will adhere adequately and not be lost on its way to the stenosed arterial segment, while still being dissolved completely on expansion of the balloon, being transferred in a sufficient amount to the vascular wall, where it remains for a long enough period of time to have an enduring effect. The standard for achieving these goals is, on the one hand, similar properties, such as those known as clinically effective paclitaxel coatings and, on the other hand, definitely longer-lasting high active ingredient concentrations in the tissue than is the case with the macrolide lactones known in the past, in particular limus substances.

This object is achieved with a balloon catheter according to claim 1 and with coating methods according to claim 6 or 7. Other preferred embodiments are derived from the dependent claims.

In other words, the object is achieved with balloon catheters having a coating on the balloon surface, comprised of at least one limus substance in crystalline form.

As in the usual sense, the term "balloon catheter" denotes angioplasty balloon catheters, i.e., balloon catheters for percutaneous transluminal angioplasty to dilate or reopen stenosed or occluded blood vessels (usually arteries, less frequently also veins) by means of balloon dilatation. Coatings for balloon catheters must adhere to the balloon en route to the stenosed and/or occluded segment of the blood vessel, i.e., while the balloon is being guided through a hemostatic valve as well as on the path through an insertion loop filled with blood and/or through a guide catheter and through proximal portions of the blood vessel and then must dispense the active ingredient to the vascular wall rapidly, while the balloon is being filled. After the operation, the balloon catheter does not remain in the body, in contrast with an implant such as a stent or an implantable or indwelling catheter.

"At least one limus substance" means that even mixtures of several limus substances are included. A single limus substance is preferably used. The limus substances (synonym: limus drugs) are preferably selected from sirolimus, everolimus, zotarolimus, biolimus, temsirolimus, myolimus, novolimus, ridaforolimus as well as tacrolimus and pimecrolimus. The sirolimus, everolimus, zotarolimus, biolimus and temsirolimus group is more preferred. The especially preferred group consists of sirolimus and everolimus. Everolimus is most preferably used as the limus substance. Sirolimus is most preferred as an alternative.

The goals defined above are achieved according to the invention surprisingly well, completely and reproducibly as well as economically: limus drugs are brought to crystallization in suitable solvents in a known way. To be able to achieve an adequate dose on the balloon surfaces, solvent mixtures of at least one polar organic solvent and at least one apolar organic solvent may be used. The apolar and polar organic solvents preferably have at least a difference in their log $K_{OW}$ of 1 ($K_{OW}$: octanol/water distribution coefficient). The polar organic solvent is understood in particular to be an organic solvent having a log $K_{OW}$ between 1.0 and +2.0, preferably between 0.5 and +1.8. The apolar organic solvents are in particular understood to be organic solvents with a log $K_{OW} \geq 3$, preferably between 3 and 6.5. Polar organic solvents are also referred to synonymously and in abbreviated form as polar solvents, and the same thing is also true of the apolar organic solvents (apolar solvents). In at least one of the solvents, preferably in the organic polar solvent, the limus substance should have a solubility of >10 mg/mL, preferably >30 mg/mL. Examples of volatile organic solvents include alcohols, acetone, ethyl acetate and chloroform. The alcohols are understood to include monovalent or polyvalent alkanols in particular, more preferably monovalent C1-C3 alkanols, most preferably methanol and/or ethanol. Other polar organic solvents include tetrahydrofuran, acetonitrile and diethyl ether. The limus substance should have only a low solubility in the other solvent(s), preferably in the apolar organic solvent, for example, with <1 mg/mL (0.001 to 0.999 mg/mL). Examples of organic solvents having a low solubility for limus substances were cited in US 20110009618 A1; they include in particular very apolar solvents such as aliphatic C6-C10 hydrocarbons, for example, cyclohexane, hexane, heptane, octane, etc. The solvents or solvent mixtures may contain water, as will be explained in greater detail below.

Preferred solvents for crystallization or for direct coating contain 20-80% by volume of a polar solvent and 80-20% by volume of an apolar solvent. Mixtures of 30-70% by volume of one of the aforementioned polar solvents and 65-35% by volume of one of the aforementioned apolar solvents are especially preferred.

The terms "polar and/or apolar organic solvent" also include mixtures of a plurality of solvents of one and/or both categories, but preferably one solvent is used per category.

A preferred pair of polar and apolar organic solvents would be, for example, ethyl acetate and heptane.

First, the limus substance can be dissolved in a polar organic solvent, for example, ethanol or other alcohols, acetone, ethyl acetate, tetrahydrofuran, acetonitrile, diethyl ether, etc. (step a) and then the solution can be mixed with the apolar solvent, so that either a supersaturated solution is formed or the true solubility is maintained (step b). In the case of a supersaturated solution, crystallization of the limus substance can be triggered by suitable measures, for example, by glass-on-glass rubbing or by adding crystal seeds (step d) or the supersaturated or true solution is applied to the balloon in the absence of crystals and is crystallized there (step c). If crystallization already occurs in solution, the suspension may be applied to the balloon surface, where it is crystallized further and/or dried (step d1) or the crystals are isolated and optionally dried (step d2). The crystals may be subjected to suitable measures to limit the size distribution. The limus crystals may be resuspended in a suitable liquid and applied to balloons, where they are crystallized further and/or dried. Liquids in which the crystals do not dissolve completely or at all are most suitable, for example, the apolar organic solvents mentioned above, mixtures thereof or aqueous solvents or solvents containing some water.

"Containing water," "aqueous" and/or "some water" all mean that water is present in the amount of 0.01 to 50% by volume, wherein the total percentage amounts of the solvent and the water by volume add up to 100. The percent by volume of water and of the polar solvent preferably add up to 20-80% by volume, more preferably 30-70% by volume, i.e., the amount of water is subtracted from the amount of polar solvent so that the total yields 100% by volume including the amount of apolar solvent.

There are various possibilities for reproducibly coating surfaces of a balloon of a balloon catheter with limus crystals:

a) Limus crystals are suspended in a solvent or solvent mixture in which the crystals are not soluble. The apolar organic solvents listed above are preferably used here as the solvents/suspension media. This suspension is applied to the balloon in a therapeutic dose.

b) Limus crystals are applied to the balloon surface as described under (a) but in a much lower subtherapeutic dose, for example, between 0.001 µg and 0.5 µg limus substance per mm² balloon surface area, preferably between 0.001 and 0.1 µg limus substance per mm² to cause seed crystals to be deposited on the balloon. Immediately thereafter or after drying the seed crystals, the balloon is coated with a largely completely saturated supersaturated limus solution until reaching a therapeutically active dose. In other words, an additional dose of the at least one limus substance is applied in the form of a solution that is at least saturated, corresponding to a dose between 1 µg and 10 µg limus substance per mm² balloon surface area (in the final dry state). Saturated or supersaturated solutions can be prepared in very different solvents, but solvent mixtures of a polar solvent (ethyl acetate, acetone, isopropanol) and an apolar solvent (for example, cyclohexane, hexane, heptane, octane), optionally with the addition of water, are preferred. The crystallization, the size of the crystals and their aggregation can be controlled by means of the drying conditions, in particular the temperature and the movement of air.

Unencapsulated microcrystals, even partially unencapsulated free microcrystals (in contrast with Miceli Technologies, US2012015442, WO2013059509) are preferred. The (free) microcrystals may be applied in a matrix to the balloon surface, so that the matrix either promotes adhesion to the balloon surface or promotes the release of the crystals of active ingredient on expansion of the balloon but not the release of the active ingredient from the capsule after it enters the tissue.

The range of therapeutically effective doses, i.e., doses that inhibit proliferation of neointima or doses that are otherwise effective, is preferably between 1 µg and 10 µg limus substance per mm² balloon surface area.

More than 30% by weight of the limus substance should be present in the form of crystals on the balloon surface, preferably more than 50% by weight, and in particular preferably more than 70% by weight. The individual crystals, the so-called microcrystals, preferably have a rhomboid shape and are variable in size, with a substantial portion of the crystals (based on the mass), i.e., >30% by weight, optionally having their greatest longitudinal extent between 1 and 300 µm, preferably >50% by weight, more preferably >80% by weight. Aggregates of single crystals, which may be larger, are formed due to the drying.

The melting point of the crystals is in the range of 171-188° C. The dwell time of the limus substances transferred from the balloon into the tissue is significantly greater in comparison with that of the known preparations. The average half-life (elimination half-life) in porcine coronary arteries is week, preferably weeks. In other words, the balloon catheter having a coating on the balloon surface containing at least one limus substance in crystalline form is characterized in that the crystals have an elimination half-life of ≥1 week, preferably ≥2 weeks within a period of 4 weeks after the treatment, after transfer from a balloon catheter into porcine arteries.

The coating may contain only the limus substance, optionally also in solvate crystals. Various excipients and/or additives may be added to the coating, but coatings without polymers are preferred, i.e., the coating is preferably free of polymers. Suitable additives/excipients include, among others, antioxidants, preferably ascorbyl palmitate, butylhydroxyanisole, butylhydroxytoluene, nordihydro-guaiaretic acid, probucol, propyl gallate, resveratrol, especially preferably butylhydroxytoluene and/or resveratrol, and most preferably resveratrol. In addition, other high- and low-molecular-weight substances that are used for coating drug-eluting balloon catheters are also suitable, such as those mentioned in U.S. Pat. No. 8,439,686, US2010/324648, US2008/0118544, U.S. Patent 2013/0123695 or conventional pharmaceutical excipients. In other words, in a preferred embodiment, the coating consists only of the limus substance, optionally also in solvate crystals, and additionally optionally excipients and/or additives such as antioxidants. In particular, polymers, for example, carrier polymers need not be present, i.e., the coating is preferably free of polymers. In another embodiment, coatings containing the limus substance only in crystal form, optionally in solvate crystals, are preferred. In other words, the coating on the balloon surface in this other preferred embodiment consists of the at least one limus substance in crystalline form, optionally in solvate crystals, i.e., no other substances are present after drying/removing all the solvents. In these other embodiments and other preferred embodiments, no polymers such as carrier polymers in particular are present.

These coatings may also be sufficiently stable for more than one year at room temperature even without the addition of antioxidants, i.e., the active ingredient content declines by less than 5% by weight over this period of time. On the other hand, various excipients can have a positive influence on the adhesion of the active ingredient to the balloon material, the release on expansion of the balloon, the transfer into the vascular wall and the efficacy and tolerability. Preferred excipients include antioxidants, preferably in amounts of >5% by weight of the limus substance, hydrophilic substances, such as X-ray contrast media, sugars and sugar alcohols, glycerol, urea preferably in weight amounts of 5-100% by weight of the limus substance, also amphiphilic substances in very small amounts, preferably ≤1% by weight of the limus substance and lipophilic substances, such as fatty acid salts, preferably in the range of 0.5-50% by weight of the limus substance.

Medicinally active substances may be used as additives.

The excipients or additives, preferably excluding polymers as mentioned above, may be used individually or in mixture. If used in mixture, the quantitative amounts indicated for the sum of excipients and/or additives shall be applicable. The excipients/additives may be added to the coating solution or they are preferably applied in advance to the balloon surface or even more preferably applied subsequently, i.e., after drying is concluded, in order not to disturb the crystal structure of the limus substances. If the excipients/additives are applied subsequently, then solvents and conditions that prevent dissolving of the limus crystals should be selected, for example, solvents in which the limus substance is sparingly soluble, readily volatile solvents, spray coatings, low temperatures. In a final step [c or e)], at least one additional layer of an additive and/or excipient is preferably applied, i.e., preferably applied in a manner such that the limus crystals are not converted to an amorphous form. Alternatively, it can be stated that, in an additional final step c or e) at least one additional layer of an additive/excipient is applied without using an agent that dissolves the limus substance.

In each of the preparation variants according to the invention, it is preferably to work without any polymer and accordingly to create a polymer-free coating.

Otherwise all conventional methods are possible for coating the balloons, such as dipping, spraying, printing, painting, microdosing methods, etc.

All dimensionally stable and expandable materials may be used as the balloon membrane, in particular polyamide/nylon, PEBAX, polyethylene, polyurethane, silicone, latex, ChronoPrene. The balloon membranes may be additionally reinforced by structures contained in the membranes (threads, strips, wires) or may be surrounded by such structures on the outside, as is the case in "scoring" or "cutting" balloons, for example.

The balloons may additionally contain premounted balloon-expandable or self-expanding stents, which are preferably uncoated. The coating on the balloons is preferably applied before assembling the stents, but may also be applied in addition or alone thereafter.

The invention will now be explained in greater detail below on the basis of examples, although it is not limited to these examples.

EXAMPLES

Example 1

100 mg everolimus was dissolved in 1 mL ethyl acetate. Then 2 mL heptane was added. The resulting crystal suspension was treated with ultrasound and was then available for coating balloon catheters. The coating on the balloons could be carried out as described above in detail or as described in the following examples.

Example 2

45 mg sirolimus+6 mg butylhydroxytoluene were dissolved in 0.5 mL ethyl acetate. Then 0.5 mL heptane was added. Crystallization of sirolimus was triggered, resulting in a mixture of a sirolimus crystal suspension in a saturated sirolimus solution. The suspension was treated with ultrasound for 30 minutes. Next the suspension was applied using a microsyringe to expanded balloons of catheters for percutaneous transluminal coronary angioplasty (Sequent®, BBraun). After coating, the balloons were folded and sterilized using EO.

Analysis: 6.8 µg sirolimus per $mm^2$ balloon surface area. X Ray diffraction and differential thermal analysis prove the crystalline structure of the active ingredient.

Example 3

The coronary arteries of young domestic pigs (body weight approximately 25 kg) were treated using balloon catheters according to Example 2. Two animals (6 treated vessels) were sacrificed approximately 10 minutes after the treatment; 11 other animals (11 treated vessels) were sacrificed after four weeks. The treated vascular segments were removed from all animals. The sirolimus content of the arteries was determined and compared with the sirolimus content of arteries from the same animals that had been treated with balloons of the same design and same coating composition and dose (45 mg sirolimus+6 mg butylhydroxytoluene, 7 µg sirolimus per $mm^2$) but in which the sirolimus was present in amorphous form. Table 1 summarizes the results. The crystalline preparation has a greatly extended dwell time in the tissue, which is very surprisin. The quantity of active agent in the tissue dropped by a factor of 80 within four weeks in the case of the amorphous preparation and identical experimental conditions, but the quantity of active ingredient decreased only by a factor of <3 in the case of the balloons coated with the crystal preparation.

Table 2 shows that the formulation according to the invention leads to extremely elevated levels of active ingredient in the vascular walls in comparison with that in the state of the art. Such persistently high tissue levels are regarded as crucial for the efficacy in prevention of restenosis.

TABLE 1

Transfer and persistence of sirolimus in the vascular wall after insufflation of coated angioplasty balloons for one minute in the coronary arteries of pigs.

| Coating | Example 2 Sirolimus, crystalline | Same composition as Example 2, but amorphous sirolimus |
|---|---|---|
| Residual sirolimus on the balloons used (acute study), [% of dose] | 2.7 ± 0.8<br>n = 6 | 9.2 ± 1.6<br>n = 6 |
| Residual sirolimus on the balloons used (4-week study), [% of dose] | 2.8 ± 0.6<br>n = 12 | 8.9 ± 2.5<br>n = 12 |
| Sirolimus in the arterial wall, 10-30 minutes after treatment [µg] [% of the dose] | 224 ± 52<br>12.5 ± 2.9<br>n = 6 | 96 ± 64<br>5.1 ± 3.4<br>n = 6 |
| Sirolimus in the arterial wall, 4 weeks after treatment [µg] [% of the dose] | 83 ± 68<br>4.7 ± 3.8<br>n = 11 | 1.2 ± 0.9<br>0.1 ± 0.0<br>n = 12 |

TABLE 2

Comparison with published data: sirolimus concentration in coronary arteries of pigs (ng/mg tissue = µg/g tissue) after treatment with sirolimus-coated balloon catheters

| | MagicTouch Concept Medical, Inc. Pharm. Liposomes Takimura et al., 2012 | Caliber Therapeutics, Inc. (nanoparticles) Terrez et al., 2012 | InnoRa/Cordis sirolimus BHT US 20100331816 | Example 2 sirolimus BHT | Same composition as in Example 2; sirolimus BHT |
|---|---|---|---|---|---|
| Physical condition | Unknown | unknown | unknown | crystalline | amorphous |
| Stent | No | no | yes | Yes | yes |
| Time after treatment | | | | | |
| immediate | 141 | 423 ± 110 | 313 ± 61 | 547 ± 139 | 219 ± 118 |
| 4 days | | 200 ± 80 | | | |
| 7/8 days | 16 | 50 ± 17 | 9.8 ± 10.4 | | |
| 14 days | 6 | | | | |
| 21 days | | 33 ± 14 | | | |
| 28/30 d | | 19 ± 10 | 8.4 ± 5.7 | 136 ± 112 | 2.2 ± 1.8 |
| Average t½ (0-4 weeks) | <1 week | <1 week | <1 week | <1 week | <1 week |

Example 4

Coronary arteries from the animals in Example 3 were treated at the same time with uncoated catheters of the same type, wherein the treatment of the arteries was randomized with respect to the sequence of the catheters and the type of arteries. Immediately after the treatment, the luminal diameter of the slightly distended coronary vascular segments was measured, then after four weeks, the measurement was repeated. The reduction in lumen diameter during the four weeks is referred to as "late lumen loss (LLL)" and characterizes the unwanted constriction of vessels due to neointima proliferation. The results are shown in Table 3.

TABLE 3

Influence of the sirolimus coating of balloon catheters on the stenosis of porcine coronary arteries after dilatation and/or injury of the vascular wall

| Catheter | Uncoated | Example 2 sirolimus BHT crystalline | Same composition as Example 2; sirolimus BHT amorphous |
|---|---|---|---|
| Dose [µg] | 0 | 6.8 | 7.1 |
| n (vessels) | 12 | 11 | 12 |
| RFD initial [mm] | 2.62 ± 0.30 | 2.57 ± 0.22 | 2.42 ± 0.19 |
| MLD post [mm] | 3.06 ± 0.19 | 2.93 ± 0.32 | 2.88 ± 0.41 |
| MLD FU [mm] | 2.36 ± 0.39 | 2.60 ± 0.32 | 2.35 ± 0.43 |
| LLL [mm] | 0.70 ± 0.35 | 0.37 ± 0.24* | 0.53 ± 0.52 |
| Diameter of stenosis | 23.0% ± 11.4% | 12.3% ± 7.8%* | 16.8% ± 18.9% |

Dose = sirolimus per $mm^2$ balloon surface area;
RFD = reference diameter of the artery (without treatment);
MLD post = minimal lumen diameter after over-distention;
MLD FU = minimal lumen diameter after 4 weeks;
*$p < 0.02$ versus the uncoated controls.

The vessels treated with crystalline sirolimus had the largest lumen diameters 4 weeks after the treatment, the lowest lumen loss and the least stenosis of the diameter.

Example 5

50 mg sirolimus was dissolved in 0.5 mL ethyl acetate. Then 0.5 mL heptane was added. After 24 hours at room temperature, crystals had formed. The sample was treated with ultrasound for 30 minutes. Then the suspension was centrifuged, the sediment was washed once with 1 mL heptane and dried. 5.6 mg crystals were suspended in 1 mL heptane. Balloons 2.5-20 µm in size were coated with 10 µL of the crystal seed suspension and immediately thereafter coated with 43 µL of a solution of 15 mg sirolimus in 1 mL ethyl acetate-heptane (1:1, v/v). After a brief drying time, balloons with a homogeneous white coating were obtained. The sirolimus was primarily in a crystalline form.

The balloon catheters treated in this way were provided with stents and tested with regard to the suppression of vascular stenosis due to proliferation of neointima in coronary arteries of young pigs, as described in Examples 3 and 4. Catheters whose balloons had not been coated were used for comparison and the coating according to Example 2, but in a different dose, was also used for comparison.

TABLE 4

Influence of the sirolimus coating of balloon catheters on the stenosis of porcine coronary arteries after dilatation/vascular wall injury; comparison of various doses and coating methods

| Catheter | Uncoated | Example 5 sirolimus BHT crystalline | Example 2 sirolimus BHT crystalline; dose reduced | Example 2 sirolimus BHT crystalline |
|---|---|---|---|---|
| Dose [µg] | 0 | 3.6 ± 0.5 | 4.0 ± 1.4 | 7.19 ± 0.58 |
| n (vessels) | 12 | 12 | 13 | 12 |
| RFD initial [mm] | 2.61 ± 0.25 | 2.84 ± 0.24 | 2.78 ± 0.20 | 2.74 ± 0.26 |
| MLD post [mm] | 3.08 ± 0.35 | 3.19 ± 0.20 | 3.21 ± 0.20 | 3.20 ± 0.22 |
| MLD FU [mm] | 2.03 ± 0.58 | 2.53 ± 0.43 | 2.45 ± 0.46 | 2.48 ± 0.51 |
| LLL [mm] | 1.05 ± 0.54 | 0.67 ± 0.49 | 0.76 ± 0.48 | 0.72 ± 0.49 |
| Stenosis of the diameter | 24.3% ± 16.9% | 9.7% ± 18.4% | 6.9% ± 21.1% | 5.2% ± 17.5% |

Dose = sirolimus per $mm^2$ balloon surface area;
RFD = reference diameter of the artery (without treatment);
MLD post = minimal lumen diameter after over-distention;
MLD FU = minimal lumen diameter after 4 weeks;
*$p < 0.02$ versus the uncoated controls.

The vessels treated with crystalline sirolimus had a larger lumen diameter, less loss of lumen and less stenosis of the diameter 4 weeks after the treatment than the vessels treated with uncoated balloon.

Crystalline sirolimus on balloon catheters reproducibly inhibits the stenosis of the coronary arteries in the pig after injury to the vascular wall. This effect is achieved even in a much lower dose than the dose used in Example 4.

Example 6

Balloons of PTCA catheters (2.5-20 mm) were coated with a low dose of sirolimus seed crystals, as described in Example 5, then with the aforementioned sirolimus solution in ethyl acetate-heptane and, after drying, with 15 µL of a solution of 15 mg probucol per mL diethyl ether. The crystalline structure of sirolimus was maintained.

The invention claimed is:

1. An angioplasty balloon catheter with a polymer-free coating on a balloon surface, comprising at least one limus substance in an un-encapsulated crystalline form, wherein the un-encapsulated crystalline limus substance was applied directly from a solvent mixture of at least one polar organic solvent and at least one apolar organic solvent.

2. The angioplasty balloon catheter according to claim 1, wherein another layer, comprising additional excipients and/or additives, excluding polymers, is applied.

3. The angioplasty balloon catheter having a polymer-free coating on the balloon surface, comprising at least one limus substance in an un-encapsulated crystalline form, according to claim 1, wherein the apolar organic solvent has a log $K_{OW} \geq 3$ and the polar organic solvent has a log $K_{OW}$ between −1.0 and +2.0.

4. The angioplasty balloon catheter having a polymer-free coating on the balloon surface, comprising at least one limus substance in an un-encapsulated crystalline form, according to claim 3, wherein the apolar organic solvent is selected from the group consisting of cyclohexane, hexane, heptane, and octane and the polar organic solvent is selected from the group consisting of methanol, ethanol, acetone, ethyl acetate, and chloroform.

5. The angioplasty balloon catheter having a polymer-free coating on the balloon surface, comprising at least one limus substance in an un-encapsulated crystalline form, according to claim 4, wherein the apolar organic solvent is heptane and the polar organic solvent is ethyl acetate.

6. The angioplasty balloon catheter according to claim 1, wherein the coating contains additional excipients and/or additives excluding polymers.

7. The angioplasty balloon catheter according to claim 6, wherein the excipients are antioxidants in amounts of >5% by weight of the limus substance.

8. The angioplasty balloon catheter according to claim 6, wherein the excipients are fatty acid salts in the range of 0.5-50% by weight of the limus substance.

9. An angioplasty balloon catheter having a polymer-free coating on a balloon surface, comprising at least one limus substance in an un-encapsulated crystalline form, wherein the un-encapsulated crystalline limus substance was applied as a suspension from a solvent mixture of at least one polar organic solvent and at least one apolar organic solvent.

10. The angioplasty balloon catheter according to claim 9, wherein another layer, comprising additional excipients and/or additives, excluding polymers, is applied.

11. An angioplasty balloon catheter having a polymer-free coating on the balloon surface, comprising at least one limus substance in an un-encapsulated crystalline form, according to claim 9, wherein the apolar organic solvent has a log $K_{OW} \geq 3$ and the polar organic solvent has a log $K_{OW}$ between −1.0 and +2.0.

12. The angioplasty balloon catheter having a polymer-free coating on the balloon surface, comprising at least one limus substance in an un-encapsulated crystalline form, according to claim 11, wherein the apolar organic solvent is selected from the group consisting of cyclohexane, hexane, heptane, and octane and the polar organic solvent is selected from the group consisting of methanol, ethanol, acetone, ethyl acetate, and chloroform.

13. The angioplasty balloon catheter having a polymer-free coating on the balloon surface, comprising at least one limus substance in an un-encapsulated crystalline form, according to claim 12, wherein the apolar organic solvent is heptane and the polar organic solvent is ethyl acetate.

14. The angioplasty balloon catheter according to claim 9, wherein the coating contains additional excipients and/or additives excluding polymers.

15. The angioplasty balloon catheter according to claim 14, wherein the excipients are antioxidants in amounts of >5% by weight of the limus substance.

16. The angioplasty balloon catheter according to claim 14, wherein the excipients are fatty acid salts in the range of 0.5-50% by weight of the limus substance.

17. A method for polymer-free coating of balloon surfaces of angioplasty balloon catheters having crystalline limus substances, comprising the following steps:
   a) dissolving at least one limus substance in a polar organic solvent to form a solution,
   b) mixing the solution from a) with an apolar organic solvent so that either a supersaturated solution is formed or a true solution is maintained,
   then either
   c) applying the supersaturated solution or the true solution to the balloon surface and crystallization
   or
   d) in the case of a supersaturated solution, dissolving the crystals of the at least one limus substance to yield a suspension that contains crystals and
   either
   d1) applying the suspension to the balloon surface and performing additional crystallization and/or drying there
   or
   d2) isolating the crystals of the at least one limus substance from the suspension with optional drying and re-suspension of the crystals in a suitable liquid and applying the re-suspension to the balloon surface and performing additional crystallization and/or drying.

18. The method for polymer-free coating of balloon surfaces of angioplasty balloon catheters according to claim 17, wherein, in an additional final step e), applying at least one additional layer of an additive/excipient except for polymers as additives and excipients.

* * * * *

UNITED STATES PATENT AND TRADEMARK OFFICE
CERTIFICATE OF CORRECTION

PATENT NO. : 9,539,369 B2  
APPLICATION NO. : 15/022597  
DATED : January 10, 2017  
INVENTOR(S) : Daniel Peters Page 1 of 1

It is certified that error appears in the above-identified patent and that said Letters Patent is hereby corrected as shown below:

In the Claims

At Column 12, Line 15, "ofmethanol," should be -- of methanol, --.

At Column 12, Line 41, "crystallization" should be -- crystallization, --.

At Column 12, Line 45, "crystals and" should be -- crystals, and --.

At Column 12, Line 49, "there" should be -- there, --.

At Column 12, Line 58, "e)," should be -- e) --.

Signed and Sealed this  
Sixth Day of June, 2017

Michelle K. Lee  
*Director of the United States Patent and Trademark Office*